(12) United States Patent
Lim

(10) Patent No.: US 12,357,528 B2
(45) Date of Patent: Jul. 15, 2025

(54) MULTI-FUNCTIONAL PORTABLE SKIN CARE DEVICE

(71) Applicant: JNL CO., LTD., Seongnam-si (KR)

(72) Inventor: Sung Woo Lim, Gwangju-si (KR)

(73) Assignee: JNL CO., LTD., Seongnam-si (KR)

( * ) Notice: Subject to any disclaimer, the term of this patent is extended or adjusted under 35 U.S.C. 154(b) by 595 days.

(21) Appl. No.: 17/890,071

(22) Filed: Aug. 17, 2022

(65) Prior Publication Data
US 2022/0387250 A1    Dec. 8, 2022

Related U.S. Application Data

(63) Continuation of application No. PCT/KR2021/006158, filed on May 17, 2021.

(30) Foreign Application Priority Data

May 17, 2021 (KR) .................. 10-2021-0063332

(51) Int. Cl.
*A61H 15/02* (2006.01)
*A61H 15/00* (2006.01)
(Continued)

(52) U.S. Cl.
CPC ......... *A61H 15/02* (2013.01); *A61H 15/0085* (2013.01); *A61H 15/0092* (2013.01);
(Continued)

(58) Field of Classification Search
CPC . A61N 1/26; A61N 1/08; A61N 1/328; A61N 1/0412; A61N 1/0452; A61N 1/327;
(Continued)

(56) References Cited

U.S. PATENT DOCUMENTS 252,180 A * 1/1882 Butler .................. A61N 1/0404
601/20
374,747 A * 12/1887 Muir .................... A61N 1/0404
200/19.18
(Continued)

FOREIGN PATENT DOCUMENTS

CN    101884586 A * 11/2010 ......... A61H 15/0092
CN    209137758 U     7/2019
(Continued)

OTHER PUBLICATIONS

International Search Report and Written Opinion for PCT International Application No. PCT/KR2021/006158 issued from International Search Authority on Feb. 14, 2022.

*Primary Examiner* — Tu A Vo

(57) ABSTRACT

A multi-functional portable skin care device includes: a roller unit including a first roller and a second roller and an insulating ring member; a connecting unit including a shaft member passing through centers of the first and second rollers and the insulating ring member, a conductive pipe coupled to the rear end of the shaft member and electrically connected to any one of the first and second rollers, and a conductive rod installed along the hollows of the conductive pipe and the shaft member and electrically connected to any one of the first and second rollers; and a main body unit connected to the roller unit, a battery installed inside the main body case, a control circuit board for controlling power supplied to the first and second rollers, a control button for selecting current supplied to the first and second rollers, and an LED display for displaying the operating state.

11 Claims, 9 Drawing Sheets

(51) Int. Cl.
*A61H 23/02* (2006.01)
*A61N 1/04* (2006.01)
*A61N 1/08* (2006.01)
*A61N 1/32* (2006.01)

(52) U.S. Cl.
CPC ....... *A61H 23/0254* (2013.01); *A61N 1/0404* (2013.01); *A61N 1/327* (2013.01); *A61H 2015/0014* (2013.01); *A61H 2015/0021* (2013.01); *A61H 2015/0071* (2013.01); *A61H 2201/0107* (2013.01); *A61H 2201/0119* (2013.01); *A61H 2201/0157* (2013.01); *A61H 2201/0188* (2013.01); *A61H 2201/10* (2013.01); *A61H 2201/105* (2013.01); *A61H 2201/5097* (2013.01); *A61H 2205/022* (2013.01); *A61N 1/0412* (2013.01); *A61N 1/0452* (2013.01); *A61N 1/08* (2013.01); *A61N 1/328* (2013.01)

(58) Field of Classification Search
CPC .. A61N 1/0404; A61H 15/02; A61H 15/0092; A61H 2015/0014; A61H 2201/10; A61H 15/00; A61H 2015/0021; A61H 2015/0007; A61H 2015/0028; A61H 2015/0035; A61H 2015/0042; A61H 2015/005; A61H 15/0085; A61H 15/0078; A61H 23/0263; A61H 2023/0272–0281; A61H 23/0254; A61H 2015/0071; A61H 2201/105; A61H 2201/0188
See application file for complete search history.

(56) References Cited

U.S. PATENT DOCUMENTS

| | | | | |
|---|---|---|---|---|
| 632,316 A * | 9/1899 | Marius | ..................... | A61N 1/02 601/20 |
| 642,849 A * | 2/1900 | Otto | ....................... | A61H 15/00 336/149 |
| 693,063 A * | 2/1902 | Preston | .................... | A61N 1/02 601/20 |
| 917,367 A * | 4/1909 | Scott | ........................ | A61N 1/02 336/107 |
| 1,289,864 A * | 12/1918 | Modern | .................... | A61N 1/02 336/136 |
| 1,728,368 A * | 9/1929 | Saxer | ..................... | A61N 1/322 601/120 |
| 1,789,758 A * | 1/1931 | Kays | ................... | A61H 15/0092 336/75 |
| 2,033,508 A * | 3/1936 | Bignon | .................. | A61N 1/322 310/69 |
| 2008/0154161 A1* | 6/2008 | Abbott | ............... | A61H 15/0092 601/129 |
| 2008/0154162 A1* | 6/2008 | Thiebaut | ................ | A61H 7/003 601/125 |
| 2009/0270772 A1* | 10/2009 | Kurosu | ............. | A61H 15/0092 601/19 |
| 2009/0270779 A1* | 10/2009 | Kurosu | ............. | A61H 15/0092 601/119 |
| 2012/0041398 A1* | 2/2012 | Wen | .................... | A61H 15/0092 604/310 |
| 2012/0109041 A1* | 5/2012 | Munz | .................. | A45D 34/041 604/20 |
| 2021/0022953 A1 | 1/2021 | Wilson | | |

FOREIGN PATENT DOCUMENTS

| | | | | |
|---|---|---|---|---|
| CN | 212262162 U | | 1/2021 | |
| CN | 112295102 A | | 2/2021 | |
| DE | 3243621 A1 | * | 5/1984 | |
| DE | 29918705 U1 | * | 12/1999 | ......... A61H 15/0092 |
| DE | 29918677 U1 | * | 2/2000 | ......... A61H 15/0092 |
| DE | 202018106346 U1 | * | 12/2018 | ............ A61N 1/328 |
| GB | 535371 A | * | 4/1941 | |
| JP | H063618 Y2 | * | 2/1994 | |
| JP | 07-036938 U | | 7/1995 | |
| JP | 2008-264507 A | | 11/2008 | |
| JP | 2009247684 A | * | 10/2009 | |
| JP | 6282049 B2 | | 2/2018 | |
| KR | 101004373 B1 | * | 12/2010 | |
| KR | 10-2013-0037903 A | | 4/2013 | |
| KR | 20130037903 A | * | 4/2013 | |
| KR | 10-1384162 B1 | | 4/2014 | |
| KR | 10-1444940 B1 | | 9/2014 | |
| KR | 10-2017-0037952 A | | 4/2017 | |
| KR | 20-0493222 Y1 | | 2/2021 | |
| WO | WO-2011004627 A1 | * | 1/2011 | ......... A61H 15/0092 |
| WO | WO-2013051751 A1 | * | 4/2013 | ........... A45D 34/041 |

* cited by examiner

MULTI-FUNCTIONAL PORTABLE SKIN CARE DEVICE

CROSS-REFERENCE TO RELATED APPLICATIONS

This application is a continuation application of pending PCT International Application No. PCT/KR2021/006158, which was filed on May 17, 2021, and which claims priority from Korean Patent Application No. 10-2021-0063332 filed on May 17, 2021. The entire contents of the aforementioned patent applications are incorporated herein by reference.

BACKGROUND

1. Technical Field

The present disclosure relates to a portable skin care device, more particularly to a multi-functional portable skin care device that uses stimulation such as electric current, light wave and vibration, to make active ingredients of cosmetics permeate into the dermal layer of the skin without damaging the skin, thereby preventing atrophy and sagging of facial muscles, improving wrinkles and restoring skin elasticity.

2. Description of the Related Art

Cosmetics are the most widely used to maintain youth and beauty by preventing the skin from losing elasticity. However, under the stratum corneum of the skin epidermis, a protective barrier is formed with a thick protein protective layer, and the epidermal and dermal layers of the skin are separated by this protein protective layer, so no matter how good cosmetics are used, the active ingredients of cosmetics do not penetrate into the dermal layer, and therefore, it is difficult to obtain the effect of skin care properly only by using cosmetics. Accordingly, various technologies for penetrating cosmetics to the dermal layer are being developed.

For example, KR Patent No. 10-1710887 discloses 'a skin stimulator for absorbing cosmetics' comprising: an accommodating portion 100 for accommodating cosmetics; a roller portion 300 on which a flow path through which the cosmetics are introduced is formed; a plurality of fine needles 400 protruding from the roller portion; and a pumping portion 200 for transferring cosmetics accommodated in the accommodating portion to the flow path, wherein when the roller portion 300 presses the skin and the fine needles 400 penetrate the epidermal layer of the skin, the cosmetic is delivered to the flow path by the pumping portion 200, and the cosmetic flows along the surface of the needle and penetrates below the epidermal layer of the skin, so that the cosmetics penetrate to the dermal layer. However, the conventional skin stimulator has a problem in that it may damage the skin because it directly pierces the skin layer using fine needles.

In order to solve this disadvantage, techniques for accelerating the absorption of cosmetics without directly damaging the skin by using electric current or far-infrared rays, infrared rays, visible light waves, vibrations or the like on the skin are being used.

For example, EP (Electroration) electroporation technology is a beauty method that promotes absorption of cosmetics by passing an electric current through the skin. Cosmetics contain high-molecular substances that are not absorbed into skin cells through cell membranes, so simply applying cosmetics to the surface of the skin is ineffective. However, when an electric current flows through the skin, the cell membrane does not pass the electric current and acts as a condenser, so an ion channel is formed so that the high-molecular substances can pass through it well.

EMS (Electrical Muscle Stimulation) electric pulse technology is a beauty method that controls muscle contraction with electrical stimulation and promotes blood circulation to increase production of elastic fibers and revitalize muscle activity. By relaxing the muscles tensed by daily facial expressions, it is very effective in preventing atrophy and sagging of the facial muscles, improving the aging of the facial muscles, and restoring the elasticity of the facial skin.

MP (Mesoporation) electroporation technology is a beauty method that gives an electric shock to the skin to form a temporary passage between cells, such that the hydrophilic ingredients of cosmetics that are not well absorbed into the skin penetrate deep into the skin. That is, electrical stimulation is applied to the skin to form a passage in the skin, and a constant current is applied to nutritional components of cosmetics in order to allow the high-molecular components to penetrate the skin by using the property that charges of the same components repel each other.

In addition, light irradiating beauty devices using a light emitting diode (LED) are also being developed. Recently, mask-type light-irradiating skin care devices that irradiate light to the face while worn on the face have been introduced, and US Patent Publication No. 2005-0070977 discloses a light-irradiating skin care device in the form of a mask worn on the face.

However, these prior patents are large in size, complicated in operation, and difficult to use, so there is a limit to satisfying various needs and convenience of general users. In addition, visiting a beauty salon or a skin care salon and having a professional take care of it is expensive in terms of time and money. And there was considerable inconvenience in using the existing light-irradiating skin care device with cosmetics while wearing it on the face.

Accordingly, there is a demand for the development of a multi-functional portable skin care device that allows users to manage their own skin relatively easily without specialized knowledge, that is easy to carry and use, and that can enhance the skin improvement effect by using stimulation such as electric current, light wave and vibration simultaneously or sequentially.

SUMMARY OF THE INVENTION

The present disclosure is to solve the problems of the prior art, and the main object of the present disclosure is to provide a multi-functional portable skin care device that is portable and convenient to use, that opens pores or micro-channels between cells without damaging the skin by using electric current, light wave and vibration, and that can enhance the effect of skin improvement by penetrating the various active ingredients of cosmetics such as whitening agents, moisturizing agents, and anti-aging to the inner skin of the human body.

The multi-functional portable skin care device according to the present disclosure, conceived to achieve the objectives above, comprises:
  a roller unit including a first roller and a second roller and an insulating ring member interposed between the first roller and the second roller;
  a connecting unit including a shaft member passing through the centers of the first and second rollers and the insulating ring member, a conductive pipe of a certain length coupled to the rear end of the shaft member and connected in the longitudinal direction and electrically connected to any one of the first and second rollers, and a conductive rod of a certain length installed in the longitudinal direction along the hollows of the conductive pipe and the shaft member and electrically connected to any one of the first and second rollers; and a main body unit including a main body case mechanically connected to the roller unit through the connecting unit, a battery installed inside the main body case and supplying electricity to the first and second rollers, a control circuit board for controlling the power supplied to the first and second rollers, a control button for selecting the current supplied to the first and second rollers, and an LED display for displaying the operating state of the first and second rollers.

In the present disclosure, the first roller and the second roller are made of a conductive material and are combined with the insulating ring member to have a cylindrical shape;

the insulating ring member includes an insulating ring interposed between the first roller and the second roller and having an outer peripheral surface in contact with the skin, a first support ring protruding from one side of the insulating ring to one side and fastened to the other side of the first roller, and a second support ring protruding from the other side of the insulating ring to the other side and is fastened to one side of the second roller; and the shaft member consists of a first shaft pipe that rotatably supports the first roller and the first support ring of the insulating ring member, and a second shaft pipe that is fastened to the rear end of the first shaft pipe, is connected in the longitudinal direction, and rotatably supports the second support ring of the insulating ring member and the second roller.

A coil spring is interposed between the rear end of the conductive pipe and one connection terminal of the control circuit board, and a bent leaf spring is interposed between the rear end of the conductive rod and the other connection terminal of the control circuit board.

In the hollows of the shaft member and the conductive pipe, a first fixing sleeve and a second fixing sleeve are installed, through which the conductive rod passes such that the conductive rod does not come into contact with the inner surfaces of the shaft member and the conductive pipe, and which are made of a material that does not conduct electricity.

At the front end of the shaft member, a fixing screw for rotatably supporting the front end of the first roller is fastened, and on the outer peripheral surface of the conductive pipe, a fixing ring for rotatably supporting the rear end of the second roller is integrally formed.

At the rear end of the conductive rod, a connecting piece made of a conductive material and having a pointed end to contact the bent leaf spring is installed.

In another embodiment of the present disclosure, one or more eccentric vibration motors are further installed in the hollow of the shaft member, and the vibration motor is connected to the control circuit board of the main body unit through a wire passing through the hollow of the conductive pipe.

In addition, it may further include a protective cover detachably coupled to the front end of the main body unit to surround and protect the roller unit, and a wireless charging cradle to which the main body unit can be vertically coupled, the wireless charging cradle having a coupling recess provided with a power transmission coil inside so that the wireless charging cradle wirelessly supplies electricity to the battery through a power receiving coil installed inside the main body unit, thereby charging the battery.

A further embodiment of the present disclosure may further include an auxiliary cover comprising a cover body made of a semi-circular tubular shape so as to surround an upper end of the roller unit, a connecting part extending a certain length backward from the rear end of the cover body, and a fixing part integrally formed at the rear end of the connecting part and surrounding the outer surface of the main body unit to fix.

In this embodiment, at the connecting part, a contact switch selectively contacting the surface of the conductive pipe installed to be exposed between the roller unit and the main body unit is installed, and the rear end of the contact switch is electrically connected to a conductive pad of a certain size installed on the outer circumferential surface of the main body case.

On the lower surface of the cover body, a plurality of light emitting diodes are arranged at regular intervals, and the light emitting diodes are electrically connected to the control circuit board of the main body unit through a wire disposed along the connecting part.

At the upper end of the cover body, an accommodating box capable of accommodating a cosmetic tube of a certain size is formed, on the lower surface of the accommodating box a plurality of supply holes for supplying cosmetics discharged from the cosmetic tube to an upper part of the roller unit are formed, and on one side of the accommodating box, a pressing means for discharging cosmetics to the outside of the cosmetic tube by pressing the cosmetic tube is further installed.

According to the multi-functional portable skin care device of the present disclosure, the roller unit is made of a cylindrical shape that is easy to be closer to the human skin, and when the two rollers of the roller unit contact the skin, an electric current is circulated through the two rollers and the skin, thereby contracting the muscles in the contact area and lifting the saggy facial muscles. In addition, by applying different electrodes to the first roller and the second roller, cosmetics applied on the surface of the skin can penetrate to the inner layer of the skin. In addition, by activating the skin layer by applying an alternating pulse, it has the effect of allowing the effective substances of cosmetics, of whitening agents such as vitamin C, as well as moisturizing agents such as hyaluronic acid and heparin, and anti-aging agents such as peptides and oligonucleotides, to penetrate into the inner layer of the skin more effectively.

In addition, the present disclosure has the effects that can be applied by freely switching between various skin care modes such as EP electroporation, EMS electric pulse and MP electroporation by selectively applying several current circulation modes according to the number of times the control button is pressed, and that allows effective ingredients of the cosmetics to penetrate to the inside of the skin by pushing the cosmetics into the temporarily opened pores or micro-channels between cells using a rotating roller.

In addition, the present disclosure has the effects of promoting absorption of cosmetics by opening pores or micro-channels between cells by further applying vibration or light wave stimulation along with electrical stimulation to the skin using the auxiliary cover, and of improving skin troubles using infrared or visible light, and removing wrinkles by restoring and improving skin elasticity.

In addition, the skin care device is generally used in bipolar mode, but it can also be used in unipolar mode for fine areas such as nasolabial folds on the face where two rollers cannot touch at the same time.

DETAILED DESCRIPTION

Hereinafter, the advantages and features of the present disclosure, and a method of achieving the same will be described with reference to the accompanying drawings through the embodiments to be described in detail later. However, a detailed description of a known technology or configuration related to the present disclosure will be omitted when it may make the subject matter of the disclosure rather unclear. In addition, the terms which will be described below are terms defined in consideration of the functions in the disclosure, and may be different according to users, intentions of the users, or customs. Therefore, the definitions of the terms should be made based on the contents throughout the specification describing the multi-functional portable skin care device according to the present disclosure. In addition, in this specification, in adding reference numbers to elements of respective drawings, it is to be noted that the same reference elements have the same reference numbers if possible even though the same reference elements are shown on different drawings.

Figure 1:
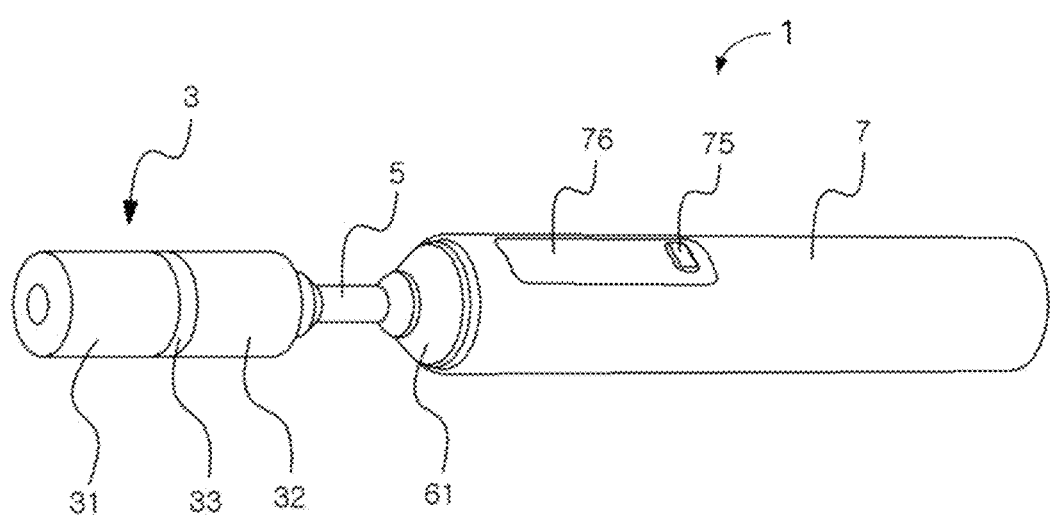
FIG. 1 is a perspective view showing a preferred embodiment of a multi-functional portable skin care device according to the present disclosure.
Figure 2:
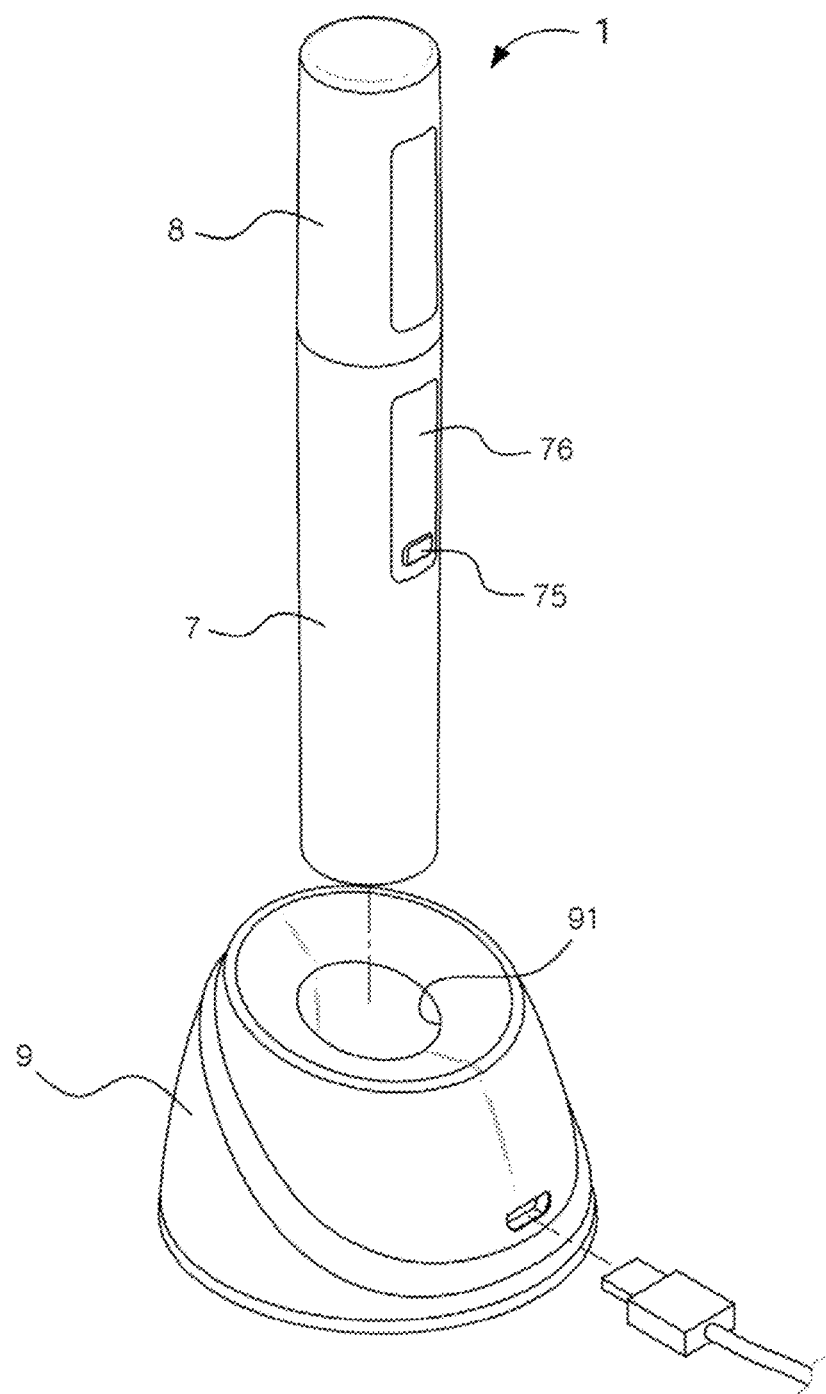
FIG. 2 is a perspective view of the multi-functional portable skin care device shown in FIG. 1, showing a state in which a protective cover is covered and a wireless charging cradle is provided.
Figure 3:
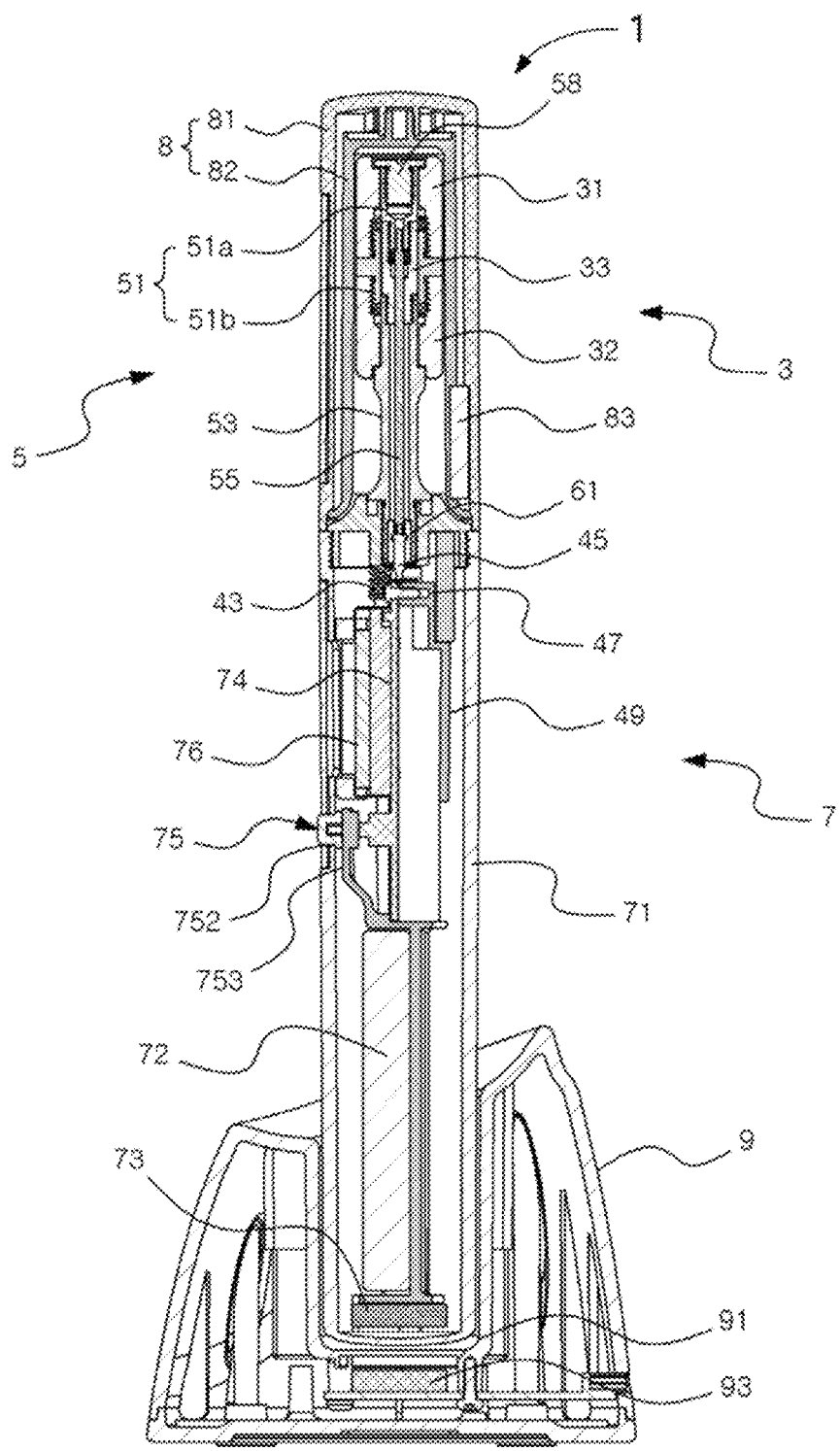
FIG. 3 is a cross-sectional view of the multi-functional portable skin care device shown in FIG. 2.
Figure 4:
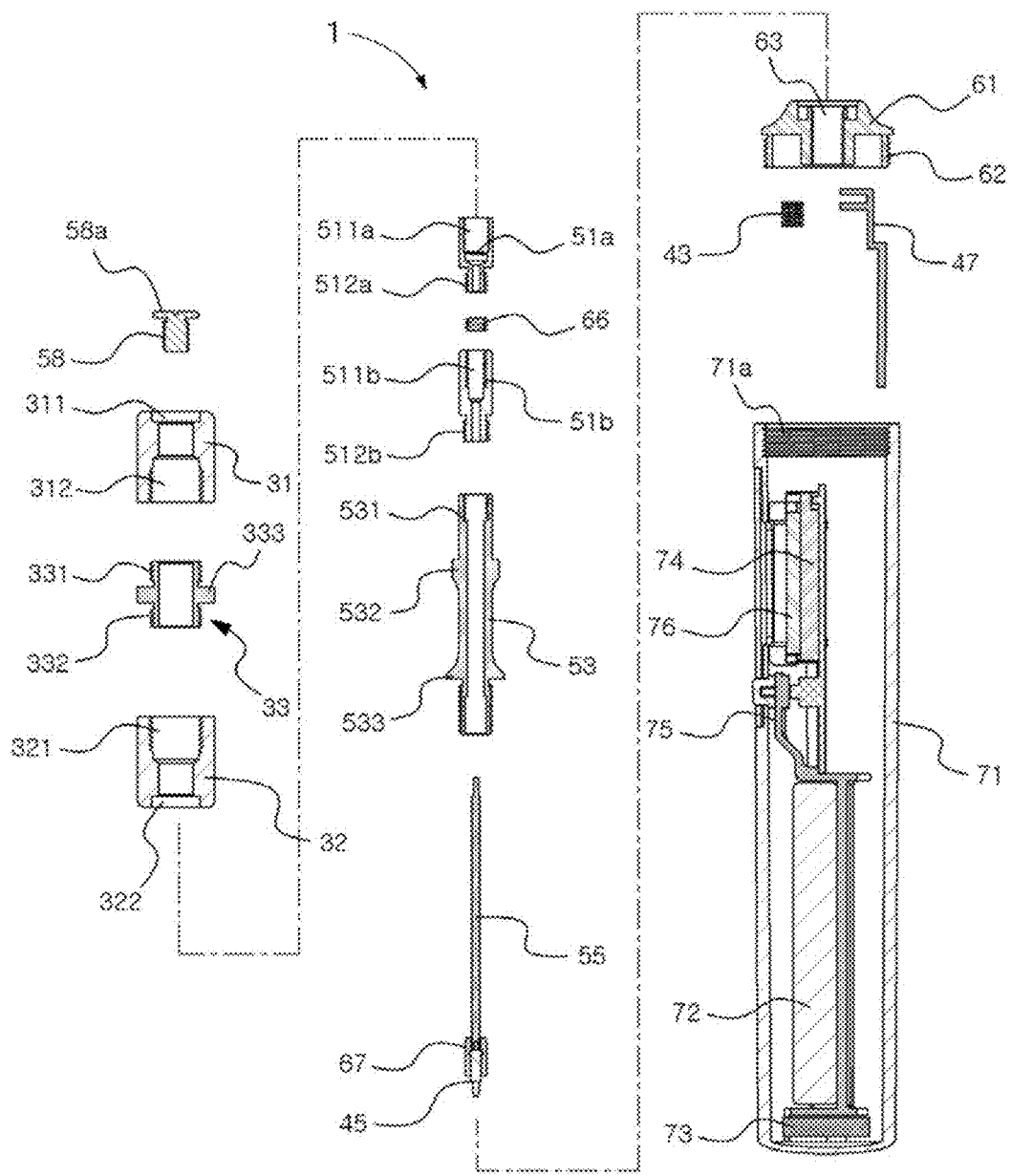
FIG. 4 is an exploded view of the multi-functional portable skin care device shown in FIG. 1.

FIG. 1 is a perspective view showing a preferred embodiment of a multi-functional portable skin care device according to the present disclosure, FIG. 2 is a perspective view of the multi-functional portable skin care device shown in FIG. 1, showing a state in which a protective cover is covered and a wireless charging cradle is provided, FIG. 3 is a cross-sectional view of the multi-functional portable skin care device shown in FIG. 2, and FIG. 4 is an exploded view of the multi-functional portable skin care device shown in FIG. 1.

FIG. 1 is a perspective view showing a preferred embodiment of a multi-functional portable skin care device according to the present disclosure, FIG. 2 is a perspective view of the multi-functional portable skin care device shown in FIG. 1, showing a state in which a protective cover is covered, FIG. 3 is a cross-sectional view of the multi-functional portable skin care device shown in FIG. 2, and FIG. 4 is an exploded view of the multi-functional portable skin care device shown in FIG. 1.

As shown, the multi-functional portable skin care device 1 of the present disclosure simultaneously or sequentially applies stimulation such as electric current, light wave and vibration to the skin to penetrate the effective ingredients of cosmetics to the inner layer of the skin without damaging the skin, thereby enhancing the effect of skin care, and it is largely composed of a roller unit 3, a connecting unit 5 and a main body unit 7. In addition, as shown in FIG. 2, the multi-functional portable skin care device 1 of the present disclosure may further include a protective cover 8 and a wireless charging cradle 9.

The roller unit 3 is a part that is in direct contact with the skin of the human body and gives an electric current, light wave and vibration to the skin, and includes a first roller 31 and a second roller 32 made of a conductive material, and an insulating ring member 33 installed between the first roller 31 and the second roller 32 and made of a material that does not conduct electricity. The roller unit 3 is made in the form of a cylindrical roller as a whole, and is installed to protrude outward from the front end of the main body unit 7 serving as a handle.

The connecting unit 5 is for electrically and mechanically connecting the roller unit 3 to the main body unit 7, and consists of a shaft member 51, a conductive pipe 53 and a conductive rod 55. Referring to FIG. 4, the shaft member 51 passes through the centers of the first roller 31, the second roller 32 and the insulating ring member 33, and rotatably support them. The conductive pipe 53 is coupled to the rear end of the shaft member 51, extended to the rear by a certain length and fixed to the main body unit 7, and has one end electrically connected to any one of the first and second rollers 31 and 32. The conductive rod 55 is installed in the longitudinal direction through the hollows of the conductive pipe 53 and the shaft member 51, and has one end electrically connected to any one of the first and second rollers 31 and 32.

The main body unit 7 serves as a handle when the roller unit 3 is used, and includes a main body case 71 having a cylindrical shape. Inside the main body case 71, a battery 72 for supplying electricity to the first and second rollers 31 and 32, a control circuit board 74 for controlling the power supplied to the first and second rollers 31 and 32, a control button 75 for selecting the current supplied to the first and second rollers 31 and 31, and a display 76 for displaying the operating states of the first and second rollers 31 and 32 are included.

As shown in FIG. 3, the protective cover 8 is a cylindrical lid detachably coupled to the front end of the main body unit 7 to surround and protect the roller unit 3, is made of a cylindrical shape with one side open, and includes an inner case 82 corresponding to the shape of the roller unit 3 and an outer case 81 covering the outside of the inner case 81.

The wireless charging cradle 9 is for charging the battery 72 by wirelessly supplying electricity to the power receiving coil 73 inside the main body unit 7, and has a coupling recess 91 of a certain size formed on the upper surface such that the main body unit 7 can be vertically erected and fixed thereto.

Specifically, the roller unit 3 is formed in a cylindrical shape by combining the first roller 31, the second roller 32 and the insulating ring member 33, the first roller 31 and the second roller 32 are made of a conductive material, and the roller unit 3 has a hollow formed such that the shaft member 51 penetrates in the longitudinal direction.

Preferably, as shown in FIG. 4, the first roller 31 has a first outer enlarged recess 311 formed at the upper end of the cylindrical body, into which a head 58a of a fixing screw 58 is inserted, and has a first inner enlarged recess 312 formed at the lower end, into which a first support ring 331 of the insulating ring member 33 is inserted. The second roller 32 has a second inner enlarged recess 321 formed at the upper end of the cylindrical body, into which a second support ring 332 of the insulating ring member 33 is inserted, and has a second outer enlarged recess 322 formed at the lower end, into which a fixing ring 532 formed on the outer circumferential surface of the conductive pipe 53 is inserted.

In addition, the insulating ring member 33 is interposed between the first roller 31 and the second roller 32, and consists of an insulating ring 333 that is in contact with the other surface of the first roller 31 and one surface of the second roller 32 and whose outer peripheral surface is in contact with the skin, a first support ring 331 formed to protrude upward from the upper surface of the insulating ring 333 and inserted into the first inner enlarged recess 312 of the first roller 31 and screwed, and a second support ring 332 formed to protrude downward from the lower surface of the insulating ring 333 and inserted into the second inner enlarged recess 321 of the second roller 32 and screwed.

The shaft member 51 of the connecting unit 5 rotatably supports the roller unit 3, the conductive pipe 53 is a hollow pipe of a certain length made of a conductive material, and is coupled to the rear end of the shaft member 51 to electrically and mechanically connect the roller unit 3 and the main body unit 7, and the conductive rod 55 is installed in the longitudinal direction along the hollow of the conductive pipe 53 and electrically connects any one of the first and second rollers 31 and 32 to the main body unit 7.

That is, the shaft member 51 consists of a first shaft pipe 51a that rotatably supports the first roller 31 and the first support ring 331 of the insulating ring member 33, and a second shaft pipe 51b that is fastened to the lower end of the first shaft pipe 51a, is connected in the longitudinal direction, and rotatably supports the second support ring 332 of the insulating ring member 33 and the second roller 32.

Preferably, the first shaft pipe 51a has a cylindrical shape so that the first roller 31 can rotate, at one end of the first shaft pipe 51a a screw thread 511a is formed on the inner surface such that the fixing screw 58 is screwed, the other end is extended outward by a certain length, and has a screw thread 512a formed on the outer circumferential surface so as to be inserted into the second shaft pipe 51b and screwed together. In addition, the second shaft pipe 51b has a cylindrical shape so that the second roller 32 can rotate, at one end of the second shaft pipe 51b a screw thread 511b is formed on the inner surface so that the first shaft pipe 51a is inserted and screwed, and at the other end a screw thread 512b is formed on the outer circumferential surface so as to be inserted into the conductive pipe 53 and screwed together.

In addition, the fixing screw 58 fastened to the front end of the first shaft pipe 51a is inserted into the first outer enlarged recess 311 of the first roller 31 installed on the shaft member 51 and rotatably supports, thereby fixing the first roller 31 so as not to be separated. In addition, the fixing ring 532 formed to protrude from the outer circumferential surface of the conductive pipe 53 is inserted into the second outer enlarged recess 322 of the second roller 32 and rotatably supports, thereby fixing the second roller 32 so as not to be separated.

In the hollows of the conductive pipe 53 and the shaft member 51, a first fixing sleeve 66 and a second fixing sleeve 67 are installed, respectively. The first fixing sleeve 66 and the second fixing sleeve 67 are made of a material that does not conduct electricity, and a through hole through which the conductive rod 55 passes is formed in the center so that the conductive rod 55 does not come into contact with the inner surfaces of the conductive pipe 53 and the shaft member 51. At this time, on the outer circumferential surface of the first fixing sleeve 66, a screw thread is formed so as to be screwed to the inner periphery of the shaft member 51.

Meanwhile, the main body case 71 is made of a cylindrical plastic molded product with one open end, and has an internal space formed such that the battery 72, the control circuit board 74, the LED display 76 and the like can be installed therein.

The battery 72 is a rechargeable battery, is charged with electricity through the power receiving coil 73, and supplies electricity to the first and second rollers 31 and 32. The control circuit board 74 controls the power supplied to the first and second rollers 31 and 32, and includes, for example, a microprocessor, a DC-DC converter, a pulse generator, a voltage booster, and a roller polarity controller, etc. The DC-DC converter converts the voltage supplied from the battery, the pulse generator generates a DC voltage, a DC pulse, an AC pulse or the like under the control of the microprocessor, the voltage booster boosts the voltage converted by the DC-DC converter, and the roller polarity controller controls the polarities of the first and second rollers 31 and 32, respectively.

In addition, a control button 75 is installed in the main body unit 7, and as a user presses the control button 75, the DC-DC converter, the pulse generator, the roller polarity controller and the like are driven. For example, the control button 75 is installed between the battery 72 and the control circuit board 74, and in accordance with the number of times the control button 75 is pressed, any one of the DC mode, the DC pulse mode, the first AC pulse mode, and the second AC pulse mode is set. The LED display 76 shows the operating state of the first and second rollers 31 and 32.

In addition, a movement pedestal 49 for preventing various parts from being damaged by vibration is installed inside the main body case 71. The movement pedestal 49 is made of a shape corresponding to the longitudinal section of the main body case 71, the control circuit board 74 and the battery 75 are fixed, and an elastic support piece 753 is also formed to support a button holder 752 installed on the upper part of the control button 75 to give an elastic force.

At an entrance of the main body case, a fixing plug 61 for fixing the connecting unit 5 is installed. The fixing plug 61 closes the entrance of the main body case 71, and the conductive pipe 53 is fixed by passing through the fixing plug 61. On the outer peripheral surface extending to the rear of the fixing plug 61, a screw thread 62 is formed so as to be screwed onto the inner surface of the main body case 71, and in the center, a through hole 63 is formed through which the conductive pipe 53 passes. In addition, the rear end of the conductive pipe 53 may be screwed to the inner peripheral surface of the through hole 63 to be fixed, and in the front part, a fixing recess is formed such that the fixing protrusion 533 formed on the outer peripheral surface of the conductive pipe 53 is inserted and fixed.

In addition, inside the main body case 71, a connector member is provided for connecting the conductive pipe 53 and the conductive rod 55 to different electrodes of the battery 75. The connector member includes a coil spring 43 installed between the rear end of the conductive pipe 53 and the control circuit board 74, and a leaf spring 47 installed between the rear end of the conductive rod 55 and the control circuit board 74. The coil spring 43 is a compression spring, and is installed between the rear end of the conductive pipe 53 and one connection terminal of the control circuit board 74. The leaf spring 47 is a leaf spring bent in a '...' shape, and is installed between the rear end of the conductive rod 55 and the other connection terminal of the control circuit board 74.

Preferably, at the rear end of the conductive rod 55, a connection piece 45 made of a material that conducts electricity well is further installed. The connection piece 45 has a pointed end so as to be in contact with the side surface of the leaf spring 47.

At the conductive rod 55, a second fixing sleeve 67 is further installed. The second fixing sleeve 67 has a cylindrical shape with a hollow in the center such that the conductive rod 55 passes through, and prevents the conductive rod 55 from coming into contact with the inner surface of the conductive pipe 53. In addition, in the shaft member 51, a first fixing sleeve 66 is installed. The first fixing sleeve 66 prevents the conductive rod 55 from contacting the inner surface of the shaft member 51, is made of a material that does not conduct electricity, in the center a through hole through which the conductive rod 55 passes is formed, and on the outer peripheral surface a screw thread is formed so as to be screwed to the shaft member 51.

Meanwhile, in the protective cover 8, a magnet 83 is disposed between the inner case 82 and the outer case 81. The magnet 83 is disposed at an edge where the protective cover 8 and the main body unit 7 meet, and at a corresponding position of the main body unit 7, a corresponding magnet that attracts the magnet 83 is installed. In addition, a cover contact sensor (not shown) may be further installed on the protective cover 8. That is, even if the control button 75 is pressed by the user's carelessness in the state in which the protective cover 8 is coupled, if it is detected by the cover contact sensor that the cover is not detached, the power-off state is continuously maintained.

The wireless charging cradle 9 is provided separately from the main body unit 7, and on the upper surface a charging recess 91 is installed to a certain depth such that the lower end of the main body unit 7 can be inserted. At a lower portion of the charging recess 91, a power transmission coil 93 is disposed to correspond to the power receiving coil 73 of the main body unit 7. Accordingly, when the wireless charging cradle 9 is connected to an external power source, and the main body unit 7 is erected and inserted, then the power transmission coil 83 automatically detects the power receiving coil 73 and wirelessly supplies power to the power receiving coil 73.

When assembling the multi-functional portable skin care device 1 according to the present disclosure, as shown in FIG. 4, the second shaft pipe 51b is fastened to the front end of the conductive pipe 53 and coupled, the first fixing sleeve 66 is inserted into the second shaft pipe 51b and fastened, and then the conductive rod 55 is inserted into the hollow of the conductive pipe 53 to penetrate the first fixing sleeve 66 and fixed, and then the first shaft pipe 51a is inserted into the front end of the second shaft pipe 51b and fastened. At this time, the conductive rod 55 is installed through the second fixing sleeve 67, and to the rear end of the conductive rod 55 the connection piece 45 is attached.

Then, the second roller 32 is coupled to the outer peripheral surface of the conductive pipe 53 so that the fixing ring 532 of the conductive pipe 53 is inserted into the second outer enlarged recess 322 of the second roller 32, the insulating ring member 33 is coupled to the outer circumferential surface of the second shaft pipe 51b such that the insulating ring 333 of the insulating ring member 33 is in close contact with the second roller 32, and the second support ring 332 of the insulating ring member 33 is fastened to the second inner enlarged recess 321 of the second roller 32.

Then, the first roller 31 is coupled to the first shaft pipe 51a so as to be positioned on the outer peripheral surfaces of the first shaft pipe 51a, and the first support ring 331 of the insulating ring member 33 is inserted and fastened into the first inner enlarged recess 312 of the first roller 31. In that case, the insulating ring 333 of the insulating ring member 33 is interposed between the first roller 31 and the second roller 32.

Then, the fixing screw 58 is screwed into a fastening recess of the first shaft pipe 51a so that the head 58a of the fixing screw 58 is inserted and fixed into the first outer enlarged recess 311 of the first roller 31, and the fixing ring 532 of the conductive pipe 53 is inserted and fixed into the second outer enlarged recess 322 of the second roller 32, so that the roller unit 7 is rotatably installed on the outer circumferential surface of the connecting unit 5 and is fixed so as not to be separated.

Then, in order to fix the rear end of the conductive pipe 53 to the main body unit 7, a fixing plug 61 is screwed to the entrance of the main body case 71 to be fixed, and then the rear end of the conductive pipe 53 is screwed through the through hole 63 of the fixing plug 61. In that case, the rear end of the conductive pipe 53 is closely connected to one connection terminal of the control circuit board 74 while compressing the coil spring 43, and the connection piece 45 installed at the rear end of the conductive rod 55 is closely connected to the other connection terminal of the control circuit board 74 while compressing the leaf spring 47.

In that case, the first roller 31 is connected to one electrode of the battery 72 through the first shaft pipe 51a, the conductive rod 55, the connection piece 45, the leaf spring 47 and the control circuit board 74, and the second roller 32 is connected to the other electrode of the battery 72 through the conductive pipe 53, the coil spring 43 and the control circuit board 74. That is, currents of different electrodes are supplied to the first roller 31 and the second roller 32, but it is insulated by the insulating ring member 33 installed between the first roller 31 and the second roller 32, so that a current does not directly flow between the first roller 31 and the second roller 32.

As such, the multi-functional portable skin care device according to the present disclosure may operate in a bipolar mode, which selectively controls DC voltage, DC pulse, AC pulse, etc. applied to the first roller 31 and the second roller 32, forms a (−) pole and a (+) pole within a short distance, and when the first roller 31 and the second roller 32 are in contact with the skin of the human body at the same time, the electric currents of different electrodes applied to the first roller 31 and the second roller 32 form a complete electric current circulation through the skin, so that according to beauty methods such as EP electroporation, EMS electric pulse and MP electric penetration, pores are opened or micro-channels are formed between the skin, and cosmetic substances such as whitening agents, moisturizing agents, and anti-aging agents penetrate deep into the inner layer of the skin, thereby improving the skin.

When only one of the first roller 31 and the second roller 32 contacts to the skin, the above-described bipolar mode cannot work, but when the user directly contacts the conductive pipe 53 with his or her finger during use, current circulation is formed through the first roller 31 and the human body, so that it can also be used in a unipolar mode.

Accordingly, when the DC mode or the DC pulse mode is set according to the number of pushes of the control button 75, the cosmetic applied to the skin surface penetrates into the inner layer of the skin in the direction from the (−) pole to the (+) pole. In addition, when the AC pulse mode is set, the (+) and (−) poles are repeatedly performed, so that the cosmetic applied to the skin surface penetrates into the inner layer of the skin more effectively. That is, when AC pulses are supplied, the polarity is alternately switched, so that the skin layer is activated, and thus cosmetic substances of whitening agents such as vitamin C, moisturizing agents such as hyaluronic acid and heparin, and anti-aging such as peptides and oligonucleotides and the like can more effectively penetrate the inner skin layer.

Figure 5:
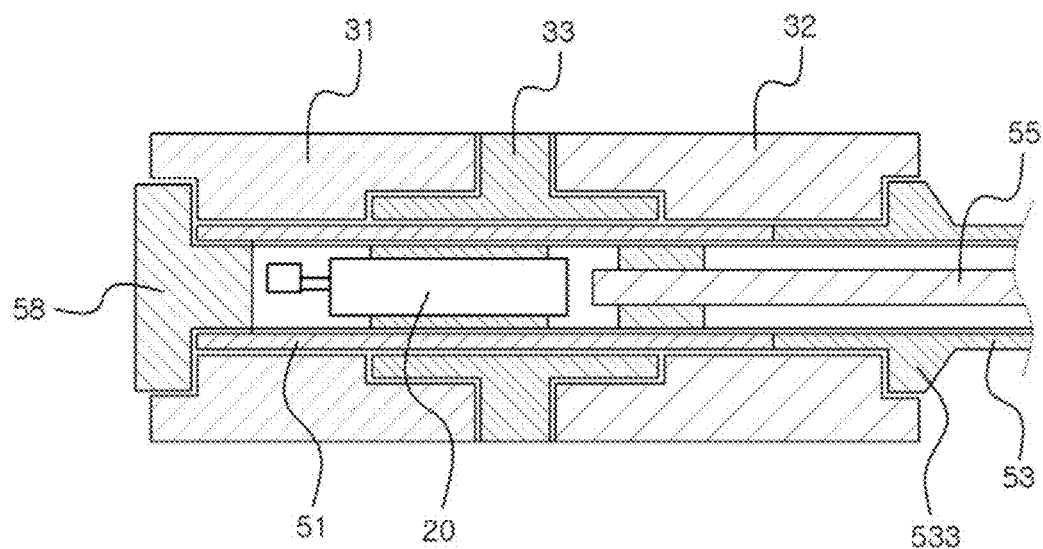
FIG. 5 is a part cross-sectional view showing another embodiment of the multi-functional portable skin care device according to the present disclosure.

Meanwhile, FIG. 5 is an enlarged cross-sectional view showing another embodiment of the multi-functional portable skin care device 1 according to the present disclosure. As shown, in this embodiment, in order to enhance the effect of skin penetration of cosmetics and give a massage effect, a small vibration motor 20 is further installed inside the roller unit 3.

Preferably, the vibration motor 20 is an eccentric motor, which is installed in the hollow of the shaft member 51 and is electrically connected to the battery 72 of the main body unit 7 by a wire disposed along the hollow of the conductive pipe 53. In addition, between the vibration motor 20 and the battery 72, a control circuit board 74 and a control button 75 may be further installed.

Accordingly, when power is applied to the vibration motor 20, the eccentric rotation shaft rotates to generate a certain vibration, and the vibration is transmitted to the skin through the first and second rollers 31 and 32. In this case, the intensity of the vibration may be applied with different intensities in proportion to the frequency of the applied DC pulse or AC pulse.

Preferably, the vibration pattern of the vibration motor 20 may be generated by adjusting the skin penetration depth of vibration based on the skin penetration rate. For example, the vibration pattern may be generated by a combination of vibration information indicating a penetration rate of 50% or more at a skin penetration depth of 2 mm or more. In this case, the vibration pattern may be a vibration pattern in which some or all of the frequency ranges of 200 to 750 Hz, 1200 to 1300 Hz, 2450 to 2520 Hz, and 2570 to 2750 Hz are combined.

Figure 6:
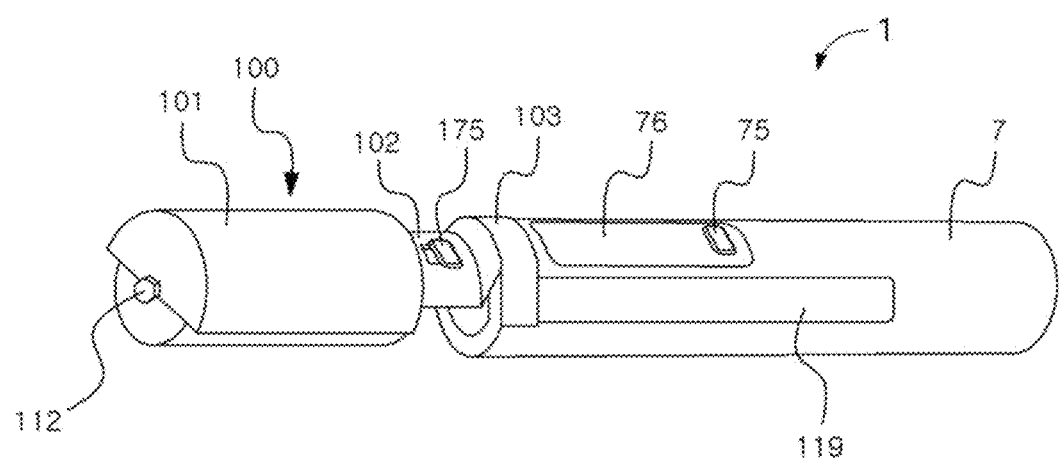
FIG. 6 is a perspective view showing a further embodiment of the multi-functional portable skin care device according to the present disclosure, showing a state in which an auxiliary cover is installed.
Figure 7:
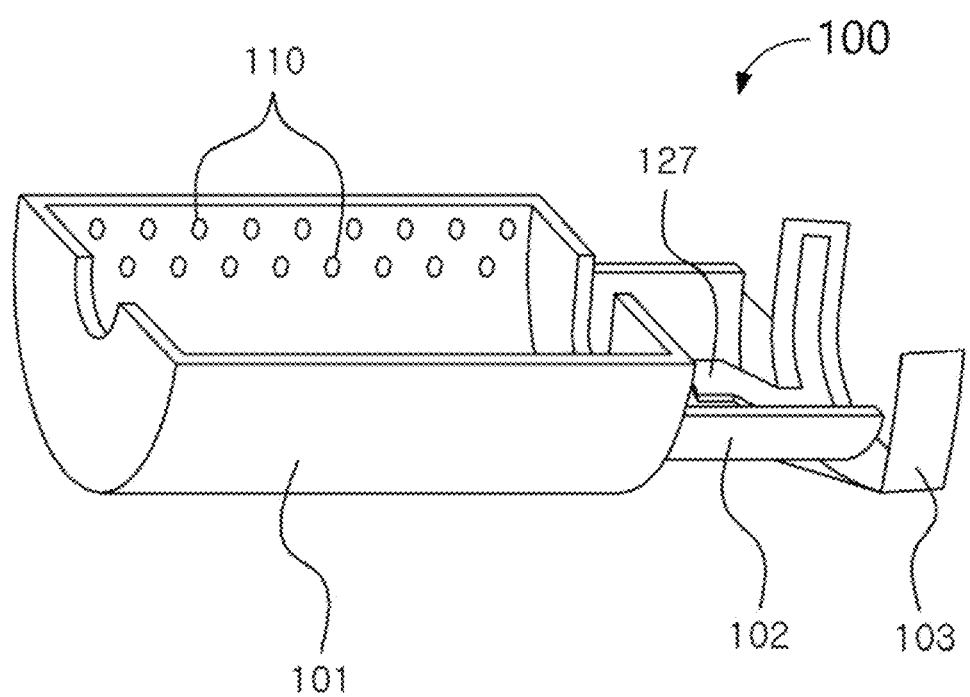
FIG. 7 is a perspective view showing a lower surface of the auxiliary cover shown in FIG. 6.
Figure 8:
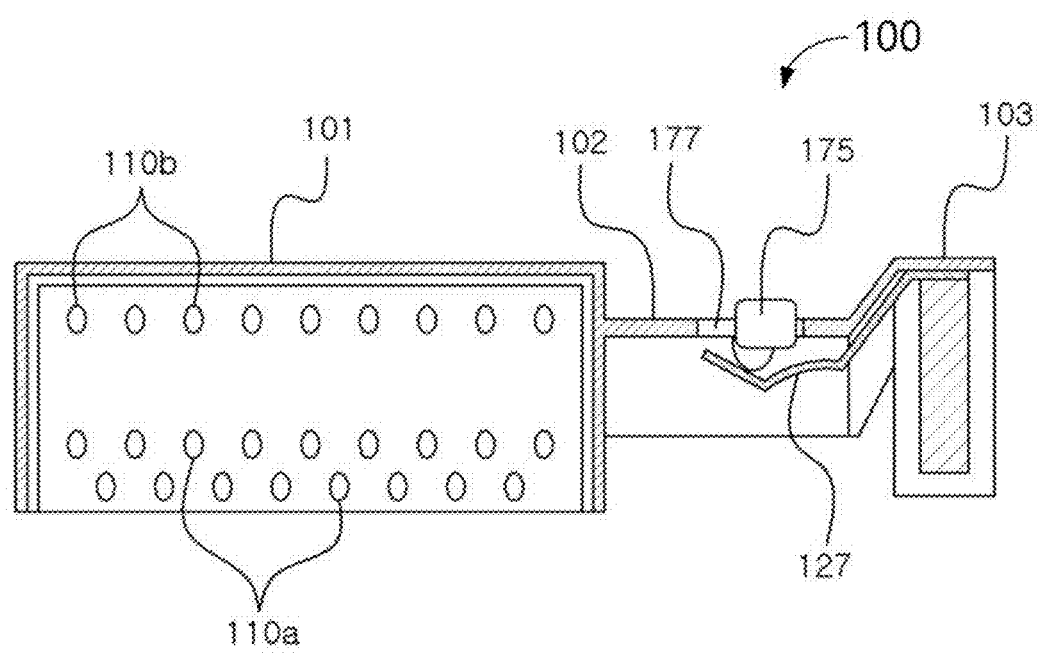
FIG. 8 is a cross-sectional view of the auxiliary cover shown in FIG. 6.
Figure 9:
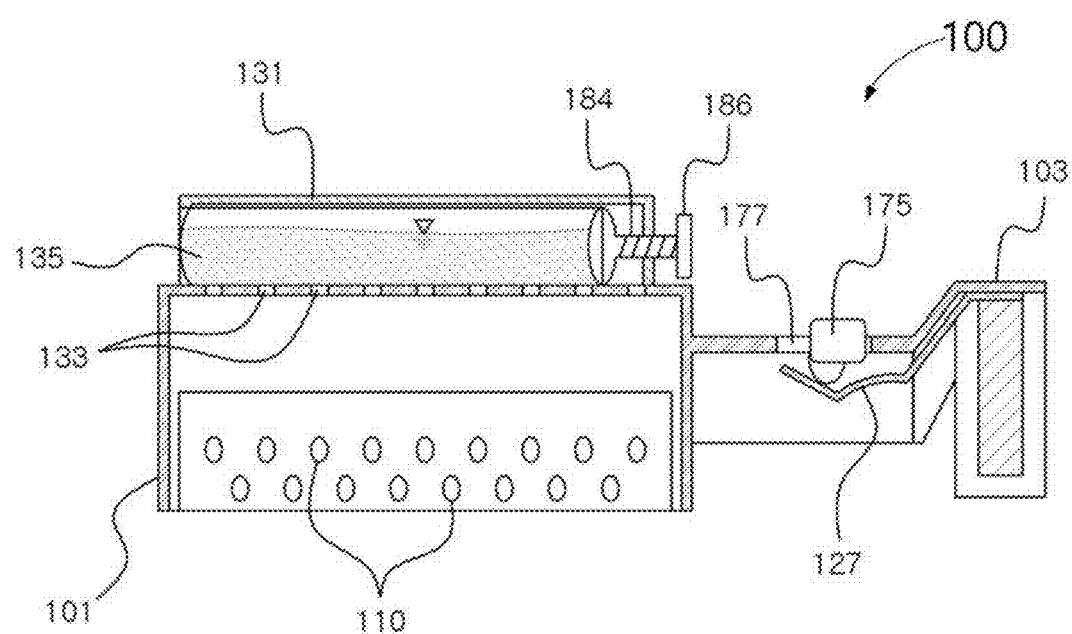
FIG. 9 is a cross-sectional view showing another embodiment of the auxiliary cover shown in FIG. 6.

FIG. 6 is a perspective view showing a further embodiment of the multi-functional portable skin care device according to the present disclosure, showing a state in which an auxiliary cover is installed, FIG. 7 is a perspective view showing a lower surface of the auxiliary cover shown in FIG. 6, FIG. 8 is a cross-sectional view of the auxiliary cover shown in FIG. 6, and FIG. 9 is a cross-sectional view showing another embodiment of the auxiliary cover shown in FIG. 6.

As shown, the multi-functional portable skin care device 1 of this embodiment includes a roller unit 3, a connecting unit 5, a main body unit 7 and an auxiliary cover 100. Since the roller unit 3, the connecting unit 5 and the main body unit 7 are the same as or similar to the above-described embodiment, the detailed description will be omitted, and hereinafter, the auxiliary cover 100 will be mainly described.

The auxiliary cover 100 is a plastic molded product, and includes a cover body 101 made of a semi-circular tubular shape surrounding the upper end of the roller unit 3, a connecting part 102 extending a certain length backward from the rear end of the cover body 101, and a fixing part 103 integrally formed at the rear end of the connecting part 102 and surrounding and detachably fixing the outer circumferential surface of the main body unit 107.

The cover body 101 has a structure in which the front and rear and upper ends are closed and the lower end is open, and forms an inner space in which the above-described cylindrical roller unit 3 can be rotatably accommodated. A fastening bolt 112 installed on the front surface of the cover body 101 is rotatably fastened to the center of the roller unit 3. For example, the fastening bolt 112 is fastened to a fastening recess of the first shaft pipe 51a to prevent the auxiliary cover 101 from being separated.

The connecting part 102 is made of a narrow width compared to the cover body 101, installed in the upper part along the conductive pipe 53 installed in the roller unit 3 and the main body unit 7, and a contact switch 175 that selectively contacts the conductive pipe 53 is installed at the connecting part 102. For example, the contact switch 175 is slidably installed in the through portion 177 formed in the connecting part 102, and when the contact switch 175 is pushed forward, an elastic contact terminal 127 installed thereunder comes into contact with the conductive pipe 53. A conductive pad 119 having a certain size is installed on the outer circumferential surface of the main body case 71, and the rear end of the elastic contact terminal 127 is connected to the conductive pad 119. Accordingly, when a user holds the main body unit 7 by hand and pushes the contact switch 175 to bring the elastic contact terminal 127 into contact with the conductive pipe 53, electricity applied to the conductive pipe 53 flows through the elastic contact terminal 127 and the conductive pad 119 into the human body, so that it can be used in a unipolar mode similarly to when the user touches the conductive pipe 53 with a finger.

As shown in FIGS. 7 and 8, on the lower surface of the cover body 101, a plurality of light emitting diodes 110 are arranged at regular intervals. The light emitting diodes 110 are connected to the battery 72 of the main body unit 7 through an unillustrated wire disposed along the connecting part 102. In addition, between the light emitting diodes 110 and the battery 72, a control circuit board 74 and a control button 75 may be further installed.

Preferably, the plurality of light emitting diodes 110 may be installed on a flexible PCB of a certain size. The wavelength band of the light emitting diodes 110 is preferably between 400 mm and 1000 mm, but is not necessarily limited thereto. It may include an ultraviolet region having a shorter wavelength or an infrared region having a longer wavelength.

In addition, the light emitting diodes 110 may all be composed of light emitting diodes emitting a single wavelength, but it is preferable to configure by mixing light emitting diodes of different wavelengths. In recent years, with the development of related technologies, by forming several diodes emitting each wavelength into one chip, it is also possible to manufacture as if several wavelengths are emitted from one light emitting diode. For example, light emitting diodes 110a of infrared or visible light may be installed on the edge of the cover body 101, and light emitting diodes 110b of ultraviolet may be installed on the edge of the cover body 101. The light emitting diodes 110b of ultraviolet may have a function of sterilizing the roller unit 3.

In addition, an optical filter plate (not shown) may be further installed on the lower surface of the cover body 101. The optical filter plate may be installed under the light emitting diodes 110a of infrared or visible light to block ultraviolet and blue light-based light. That is, in the case of a white LED, a lot of blue light-based light with a low wavelength range is included, and such blue light-based light penetrates deep into the skin and generates active oxygen, which active oxygen destroys cell membranes and causes more melanin to be produced in the cells. In addition, it is also possible to install a plurality of light emitting diodes along the border of the cover body 101.

As shown in FIG. 9, at the upper end of the cover body 101, an accommodating box 131 for accommodating a cosmetic tube 135 of a certain size is further formed. The cosmetic tube 135 may be made of a thin plastic material, and after being inserted into the accommodating box 131 in a sealed state, a part of the cosmetic tube 135 is opened to discharge the cosmetics to the outside. On the lower surface of the accommodating box 131, a plurality of supply holes 133 are formed so as to supply the cosmetics discharged from the cosmetic tube 135 to an upper surface of the roller unit 3 inside the cover body 101.

In addition, on one side, for example, on the rear end, of the accommodating box 131, a pressing means may be further installed which presses the cosmetic tube 135 to discharge cosmetics in the cosmetic tube 135 to the outside. For example, the pressing means includes a pressing part 183 for pressing the rear end of the cosmetic tube 135, a screw shaft 184 connected to the pressing part 183 and having a threaded outer circumferential surface, and a handle 186 fixed to the rear end of the screw shaft 184. At this time, the screw shaft 184 passes through the fastening groove formed on the rear surface of the accommodating box 131. Accordingly, when the handle 186 is turned and the screw shaft 184 is rotated, the pressing part 183 advances and presses the rear end of the cosmetic tube 135, so that the cosmetics inside are discharged to the outside.

As such, the multi-functional portable skin care device 1 according to the present embodiment is easy to carry, has a beautiful appearance, and is convenient to use. In addition, the multi-functional portable skin care device 1 emits electric current to the skin through the first roller 31 and the second roller 32 to mimic the action potential of the central nervous system to contract muscles of the contact area and lift saggy facial muscles. The multi-functional portable skin care device 1 may apply different electrodes to the first roller 31 and the second roller 32, so that the cosmetic applied to the skin surface penetrates into the inner layer of the skin in the direction from the (−) pole to the (+) pole. In addition, when AC pulses are supplied, the polarity is alternately switched, so that the skin layer is activated, and thus cosmetic substances of whitening agents such as vitamin C, moisturizing agents such as hyaluronic acid and heparin, and anti-aging such as peptides and oligonucleotides and the like can more effectively penetrate the inner skin layer.

In addition, the present disclosure can adapt to various skin care needs by freely switching between various skin care modes such as EP electroporation, EMS electric pulse and MP electroporation by selecting several current circulation modes according to the number of times the control button is pressed, and allows the effective ingredients of the cosmetics to penetrate to the inside of the skin by pushing the cosmetics into the temporarily opened pores or channels between cells using a cylindrical rotating roller that is easy to be closer to the skin.

In addition, the present disclosure is further provided with an auxiliary cover 100, thereby having the effects of promoting absorption of cosmetics by applying vibration or light wave stimulation along with electrical stimulation to the skin and thus giving a massage effect and at the same time by opening pores or micro-channels between cells, and of improving skin troubles by using infrared or visible light, and improving wrinkles by restoring skin elasticity.

The embodiments of the present disclosure described above have been introduced for the purpose of illustration; therefore, it should be understood by those skilled in the art that modification, change, substitution, or addition to the embodiments is possible without departing from the technical principles and scope of the present disclosure defined by the appended claims.

What is claimed is:

1. A multi-functional portable skin care device, comprising:
   a roller unit including a first roller and a second roller and an insulating ring member interposed between the first roller and the second roller, wherein the insulating ring member is configured to electrically isolate the first roller and the second roller such that electrical current does not directly flow between the first roller and the second roller;
   a connecting unit including a shaft member passing through centers of the first roller, the second roller and the insulating ring member, a conductive pipe coupled to a rear end of the shaft member and connected in a longitudinal direction and the conductive pipe electrically connected to the second roller, and a conductive rod installed in the longitudinal direction along a hollow of the conductive pipe and a hollow of the shaft member and the conductive rod is electrically connected to the first roller; and
   a main body unit including a main body case mechanically connected to the roller unit through the connecting unit, the main body unit including a battery installed inside the main body case and supplying electricity to the first and second rollers, a control circuit board for controlling a power supplied to the first and second rollers, a control button for selecting a current supplied to the first and second rollers, and an LED display for displaying an operating state of the first and second rollers, wherein a first electrode of the battery is connected to the first roller by the conductive rod and a second electrode of the battery is connected to the second roller by the conductive pipe;
   wherein the first roller and the second roller are made of a conductive material and are combined with the insulating ring member to have a cylindrical shape; wherein the insulating ring member includes an insulating ring interposed between the first roller and the second roller and having an outer peripheral surface configured to be in contact with skin, a first support ring protruding from one side of the insulating ring and fastened to one side of the first roller, and a second support ring protruding from a second side of the insulating ring and is fastened to one side of the second roller; and the shaft member consists of a first shaft pipe that rotatably supports the first roller and the first support ring of the insulating ring member, and a second shaft pipe that is fastened to a rear end of the first shaft pipe, the second shaft pipe is connected in the longitudinal direction relative to the first shaft pipe, and the second shaft pipe rotatably supports the second support ring of the insulating ring member and the second roller.

2. The multi-functional portable skin care device according to claim 1,
   wherein a coil spring is interposed between a rear end of the conductive pipe and one connection terminal of the control circuit board, and a bent leaf spring is interposed between a rear end of the conductive rod and a second connection terminal of the control circuit board.

3. The multi-functional portable skin care device according to claim 2,
wherein in the hollow of the shaft member and the hollow of the conductive pipe, a first fixing sleeve and a second fixing sleeve are installed, the conductive rod passes through the first fixing sleeve and the second fixing sleeve such that the conductive rod does not come into contact with inner surfaces of the shaft member and the conductive pipe, and the first fixing sleeve and the second fixing sleeve are made of a material that does not conduct electricity.

4. The multi-functional portable skin care device according to claim 3,
wherein at a front end of the shaft member, a fixing screw for rotatably supporting a front end of the first roller is fastened, and on an outer peripheral surface of the conductive pipe, a fixing ring for rotatably supporting a rear end of the second roller is integrally formed.

5. The multi-functional portable skin care device according to claim 4,
wherein at the rear end of the conductive rod, a connecting piece made of a conductive material and having a pointed end configured to contact the bent leaf spring is installed.

6. The multi-functional portable skin care device according to claim 5,
wherein in the hollow of the shaft member, one or more eccentric vibration motors are installed, and the one or more vibration motors are connected to the control circuit board of the main body unit through a wire passing through the hollow of the conductive pipe.

7. The multi-functional portable skin care device according to claim 6,
wherein the device further includes a protective cover detachably coupled to a front end of the main body unit to surround and protect the roller unit, and a wireless charging cradle is configured to vertically coupled to the main body unit, the wireless charging cradle having a coupling recess provided with a power transmission coil inside so that the wireless charging cradle wirelessly supplies electricity to the battery through a power receiving coil installed inside the main body unit.

8. The multi-functional portable skin care device according to claim 7,
wherein the device further includes an auxiliary cover comprising a cover body made of a semi-circular tubular shape to surround an upper end of the roller unit, a connecting part extending backward from a rear end of the cover body, and a fixing part integrally formed at a rear end of the connecting part and surrounding an outer surface of the main body unit to fix the auxiliary cover to the main body unit.

9. The multi-functional portable skin care device according to claim 8,
wherein at the connecting part, a contact switch selectively contacting a surface of the conductive pipe installed to be exposed between the roller unit and the main body unit, and a rear end of the contact switch is electrically connected to a conductive pad installed on an outer circumferential surface of the main body case.

10. The multi-functional portable skin care device according to claim 9,
wherein on a lower surface of the cover body, a plurality of light emitting diodes are arranged at regular intervals, and the light emitting diodes are electrically connected to the control circuit board of the main body unit through a wire disposed along the connecting part.

11. The multi-functional portable skin care device according to claim 10,
wherein at an upper end of the cover body, an accommodating box capable of accommodating a cosmetic tube is formed, on a lower surface of the accommodating box a plurality of supply holes for supplying cosmetics discharged from the cosmetic tube to an upper part of the roller unit are formed, and on one side of the accommodating box, a pressing means is installed, the pressing means is for discharging cosmetics to outside of the cosmetic tube by pressing the cosmetic tube.

* * * * *